United States Patent [19]

Kosaka et al.

[11] 3,934,267
[45] Jan. 20, 1976

[54] VITAL PHENOMENON RECORDING AND/OR REPRODUCING DEVICE

[76] Inventors: Shinya Kosaka, No. 1261, Wada, Tama, Tokyo; Kenji Furuta; Akira Nakayama, both of No. 1847-1, Ohwada, Hachioji, Tokyo, all of Japan

[22] Filed: Mar. 26, 1975

[21] Appl. No.: 562,335

Related U.S. Application Data

[63] Continuation of Ser. No. 374,955, June 29, 1973, abandoned.

[30] Foreign Application Priority Data

| June 30, 1972 | Japan | 47-65753 |
| July 7, 1972 | Japan | 47-77424[U] |
| July 7, 1972 | Japan | 47-67561 |
| July 7, 1972 | Japan | 47-79698[U] |

[52] U.S. Cl. ............... 360/6; 128/2.06 G; 360/137
[51] Int. Cl.² .... G11B 5/04; G11B 1/00; A61B 5/04
[58] Field of Search .............. 360/6, 27, 55, 60, 90, 360/137; 128/2.06 G

[56] References Cited
UNITED STATES PATENTS

| 3,499,124 | 3/1970 | Wortzman | 360/6 |
| 3,521,010 | 7/1970 | Sato | 360/137 |
| 3,651,280 | 3/1972 | Streckmann | 128/2.06 G |
| 3,710,035 | 1/1973 | Tupaj et al. | 360/137 |
| 3,727,012 | 4/1973 | Cox et al. | 360/27 |

*Primary Examiner*—Robert S. Tupper
*Attorney, Agent, or Firm*—Haseltine, Lake & Waters

[57] ABSTRACT

A vital phenomenon recording and/or reproducing device such as an electrocardiograph, an electromyograph, an electroencephalograph, etc. comprises a main unit including at least a magnetic tape driving mechanism and a magnetic head, a recording attachment capable of being detachably connected to said main unit mechanically and electrically, and a reproducing attachment capable of being detachably connected to said main unit, to said recording attachment being connected a detector such as electrodes to be adhered to a body of a patient and to said reproducing attachment being connected a recorder, for example, an XY recorder. Between said main unit and the recording attachment or between said main unit and said reproducing attachment, there may be detachably interposed additional attachments comprising a preamplifier, a battery checking circuit, a calibration voltage producing circuit, a transmitter, an automatic starting circuit, a battery for energizing a bridge circuit of a wire resistance strain gauge, etc. or a suitable combination thereof.

15 Claims, 15 Drawing Figures

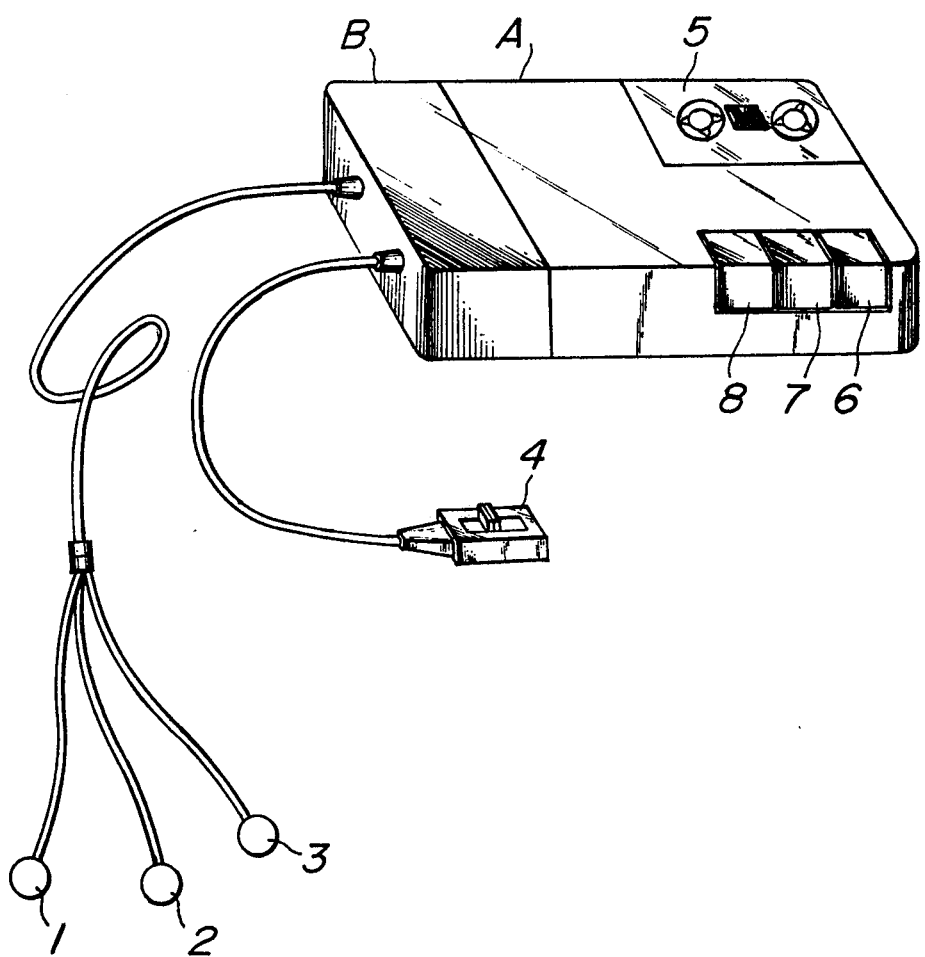
FIG_1

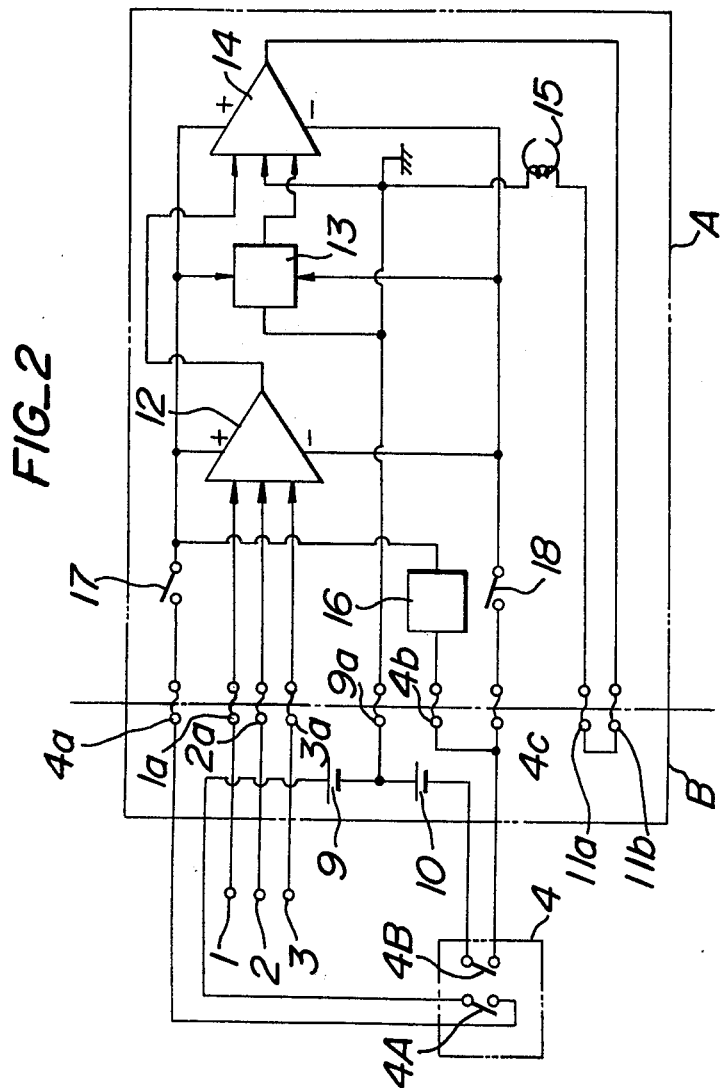

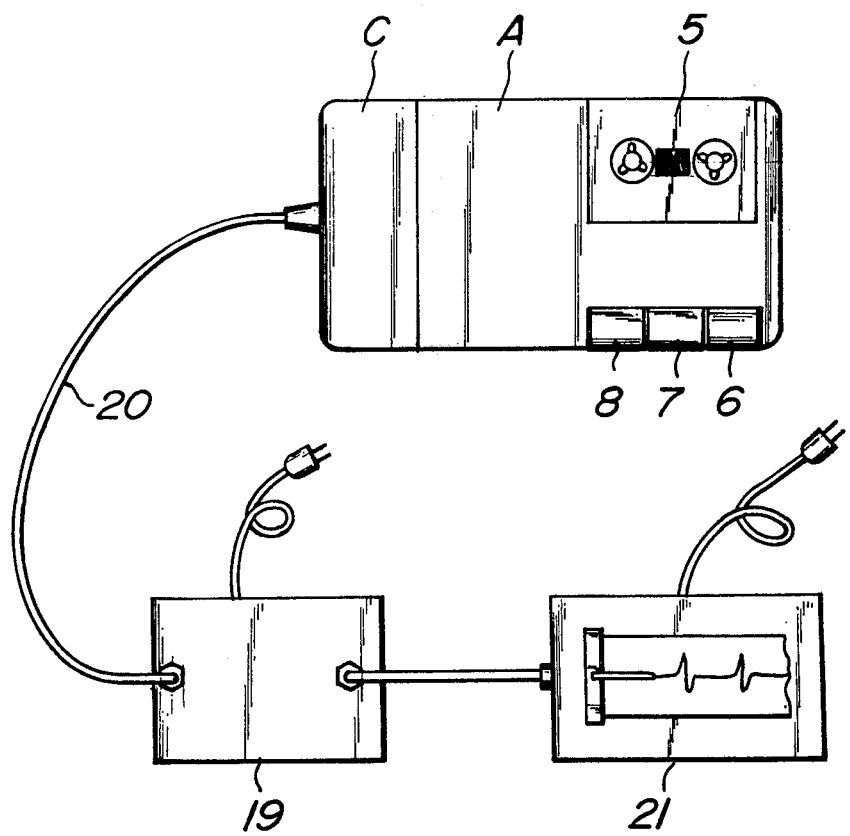
FIG_3

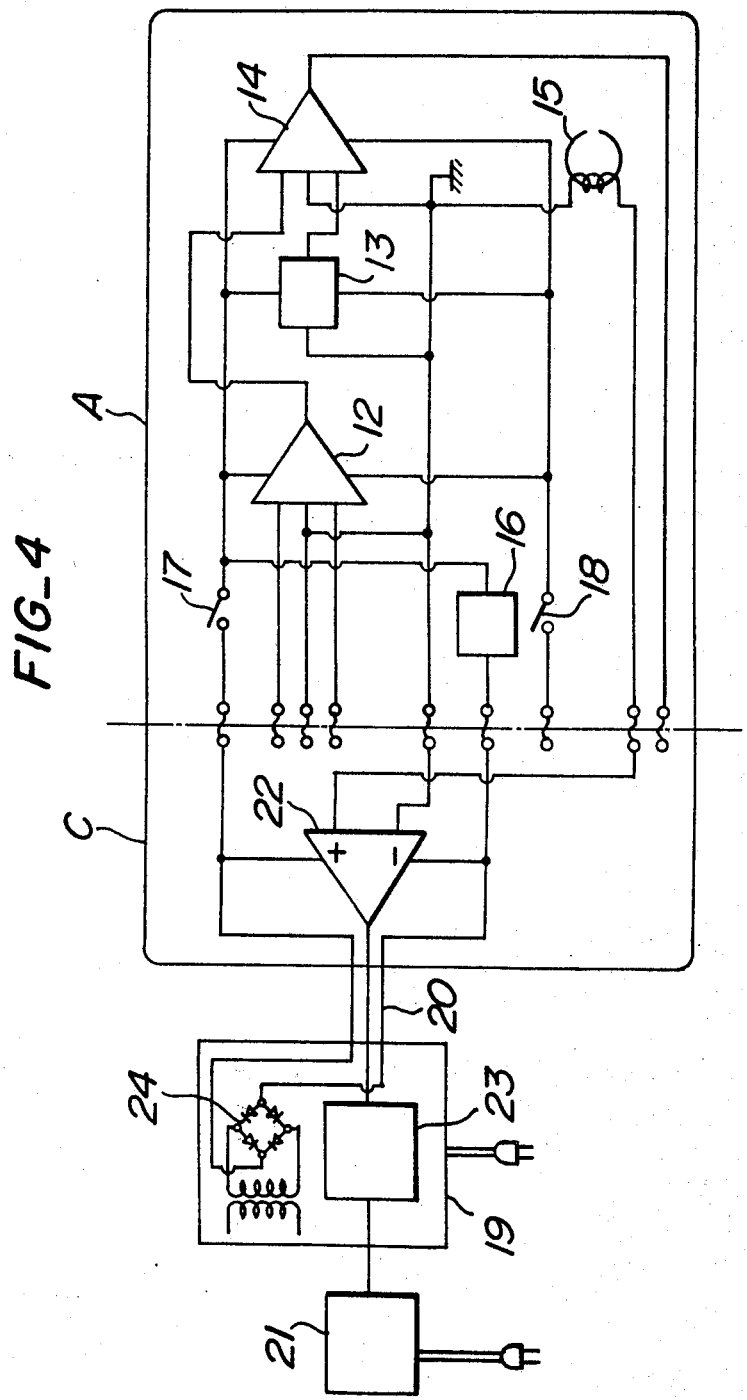

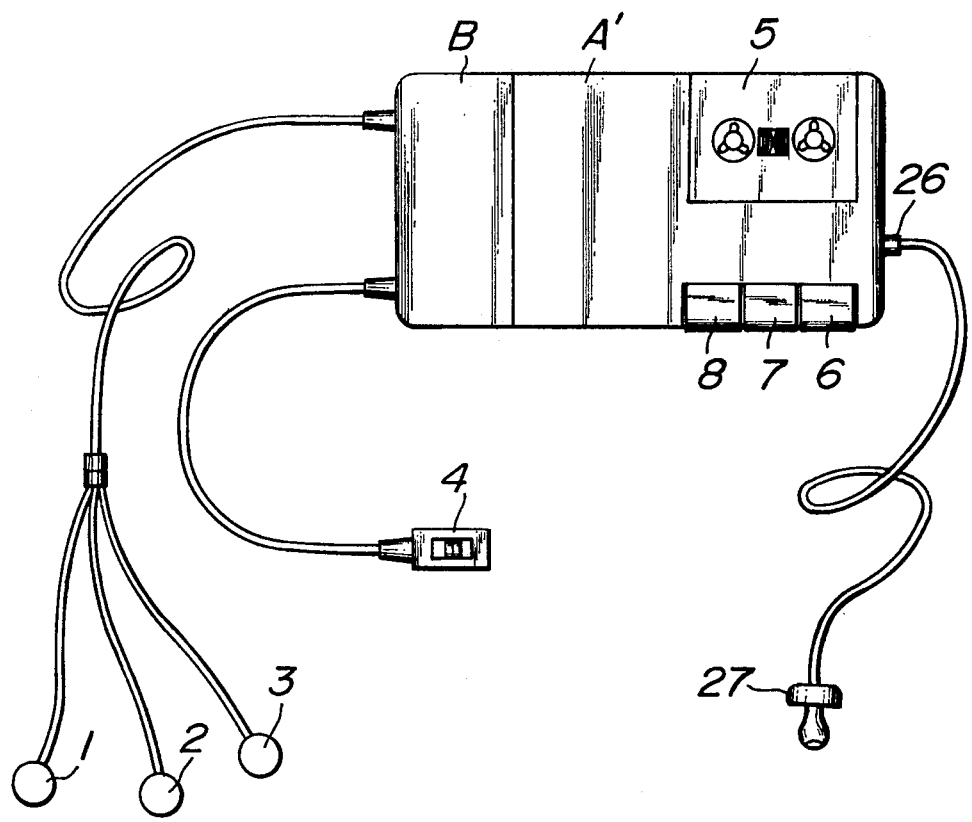

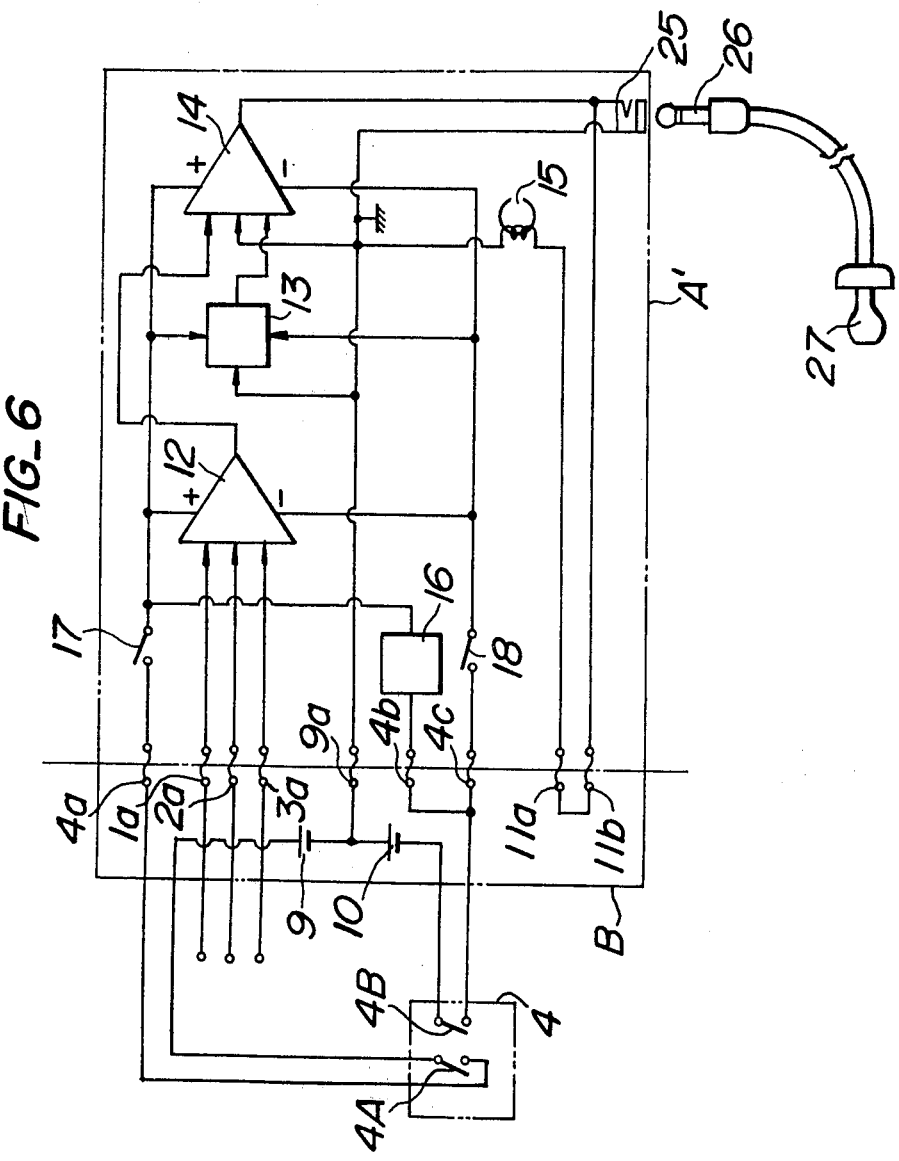

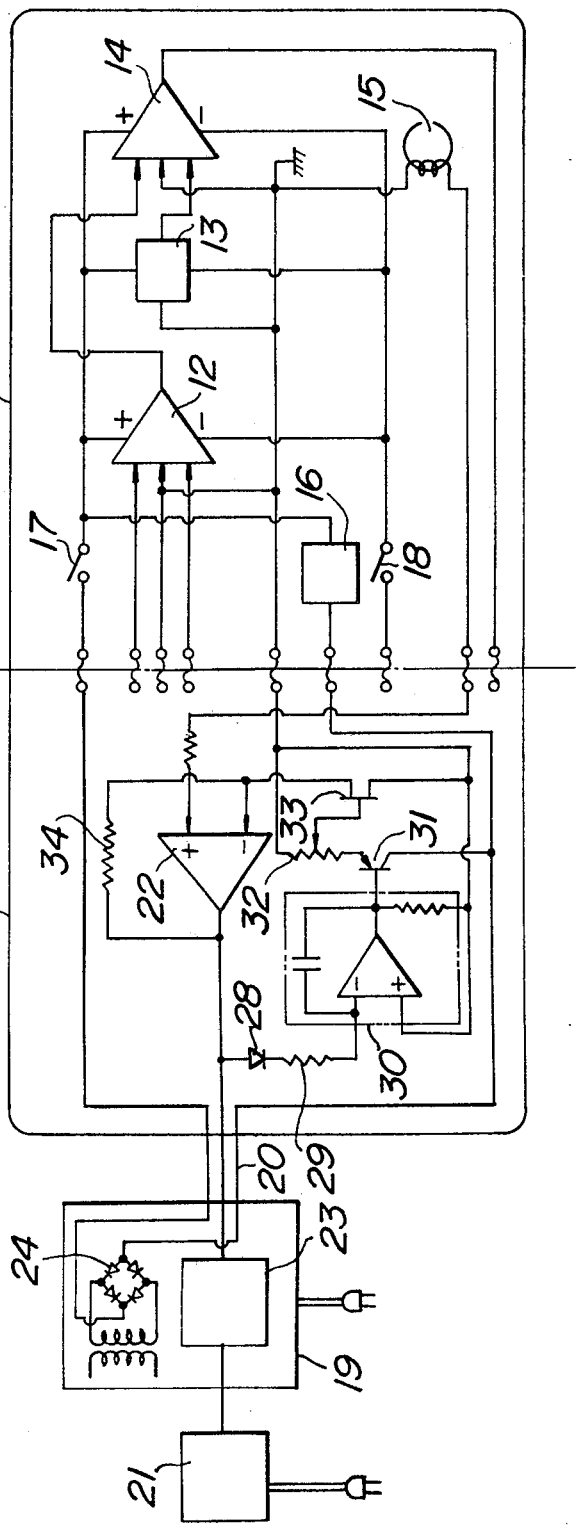
FIG_7

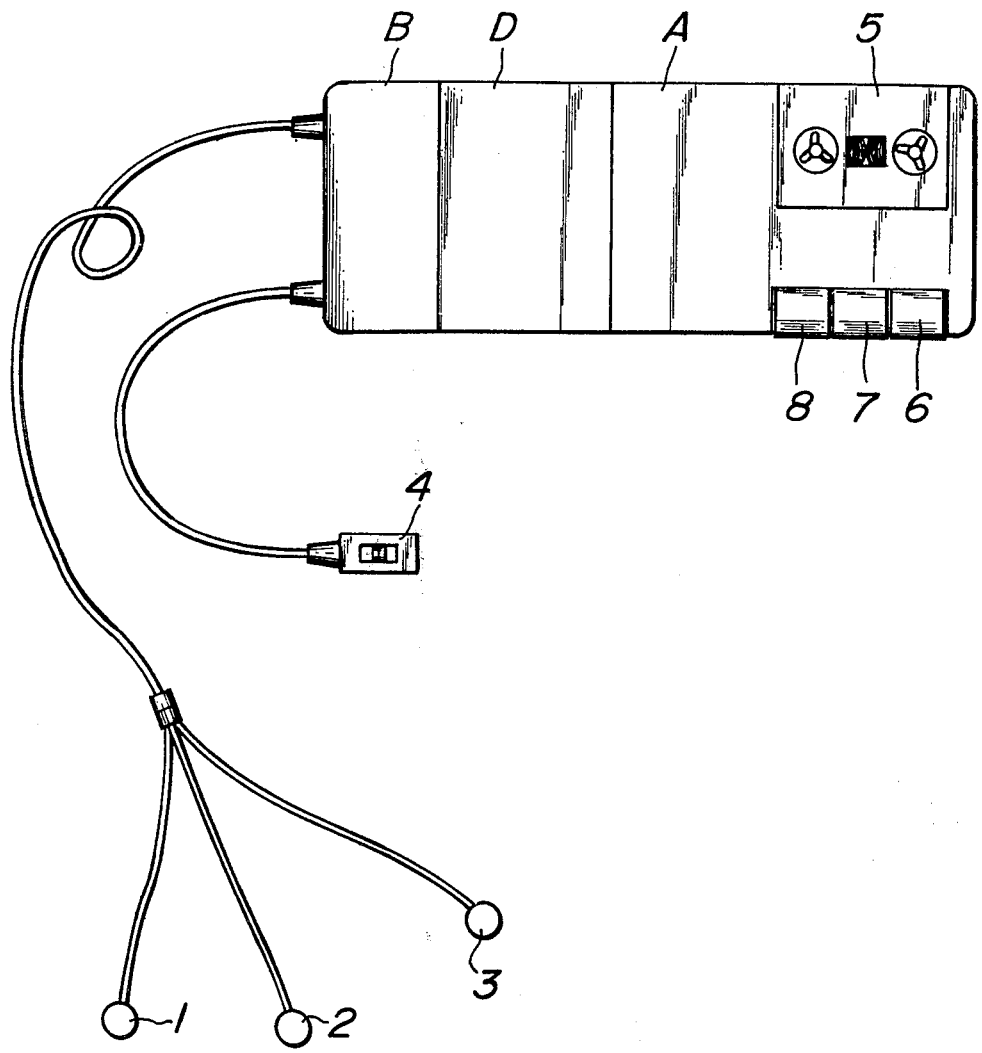
FIG_8

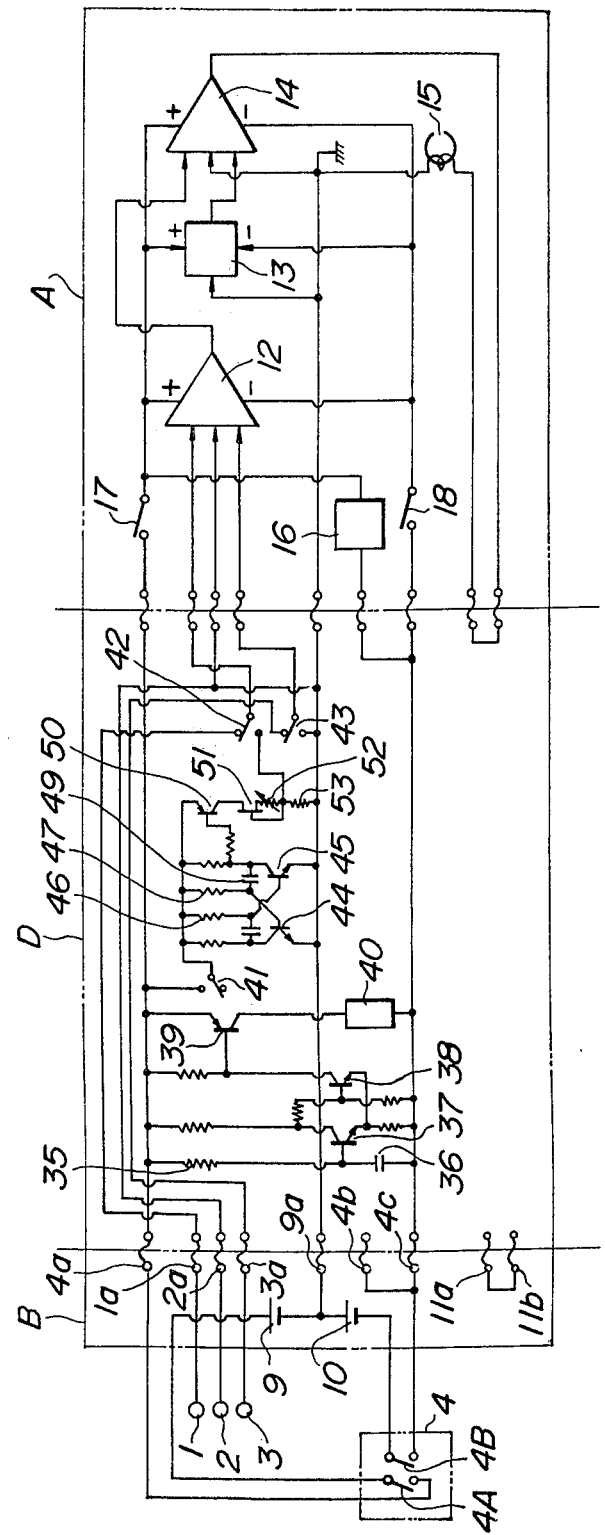
FIG_9

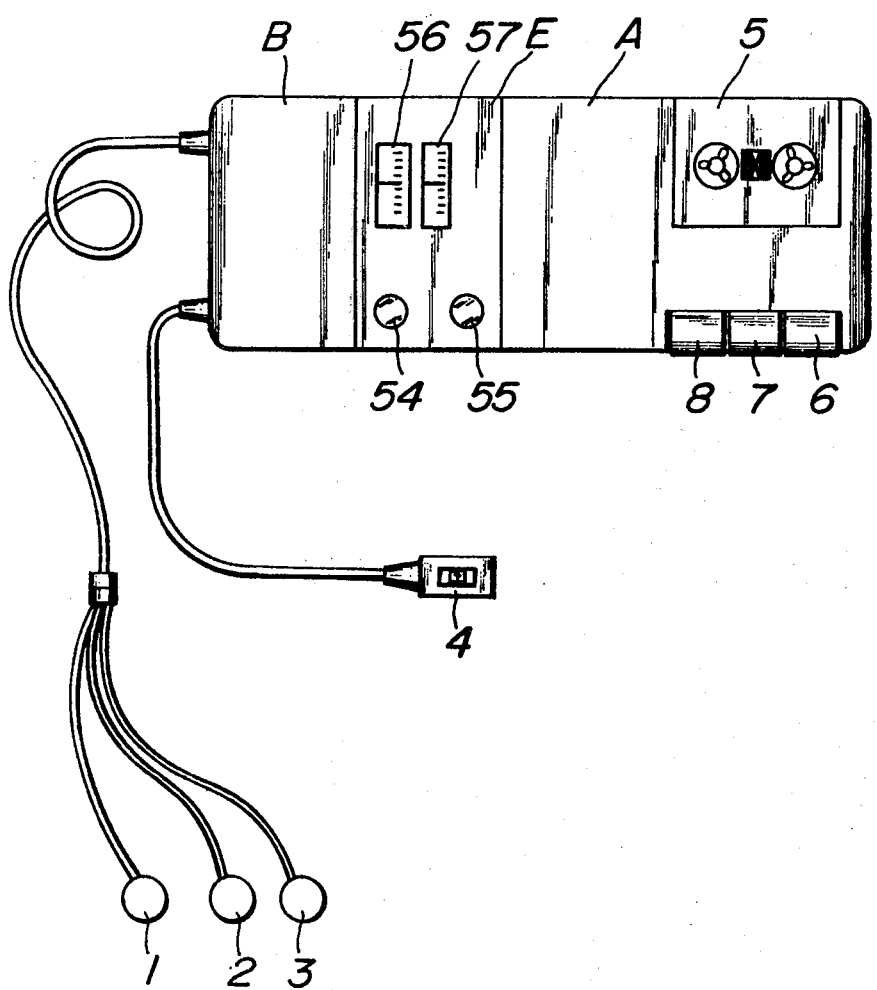

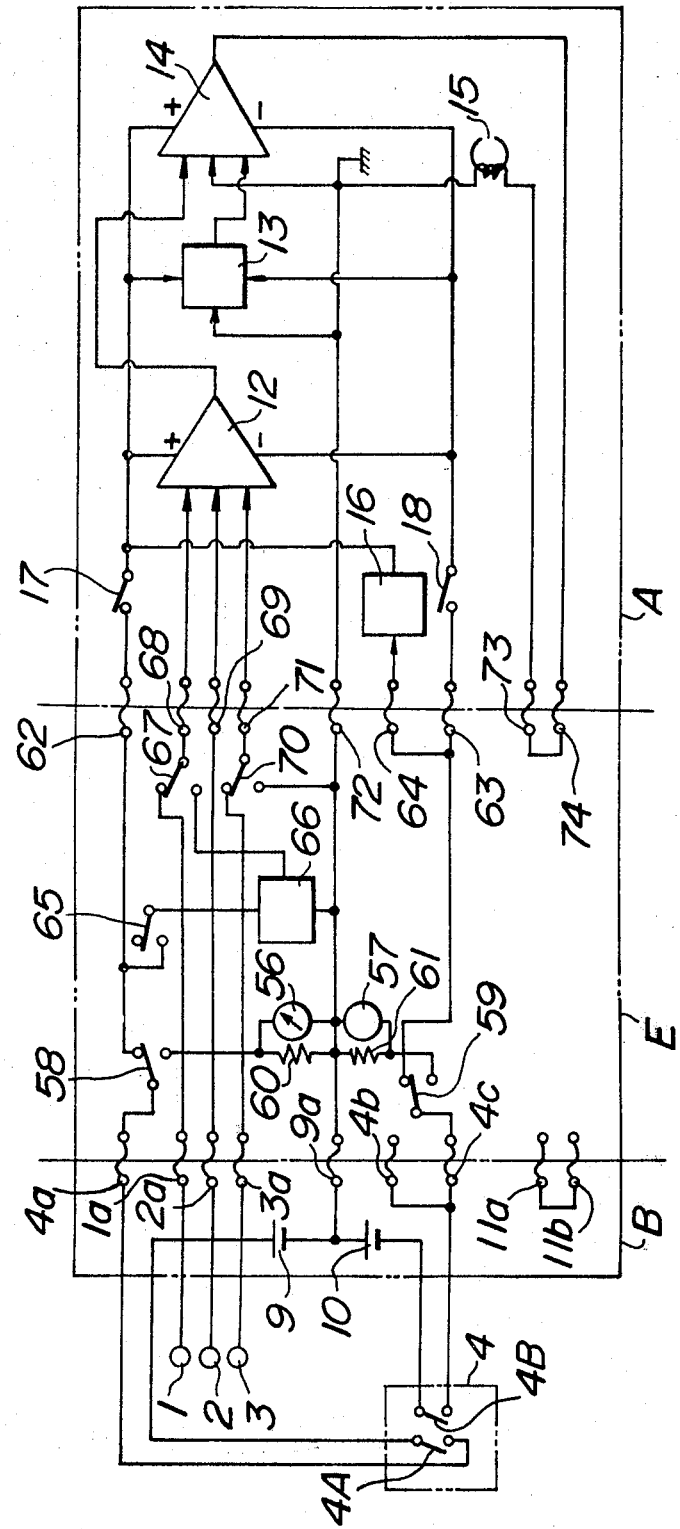
FIG_11

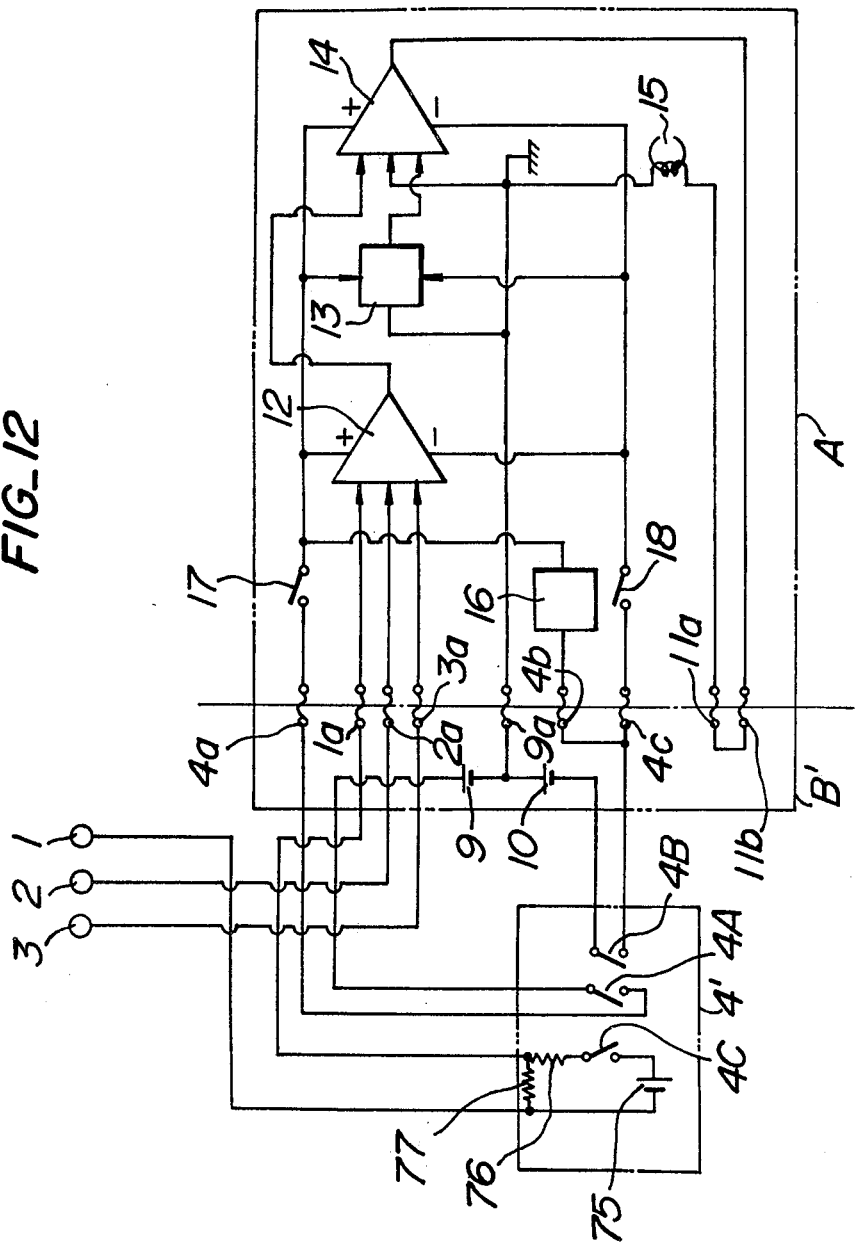

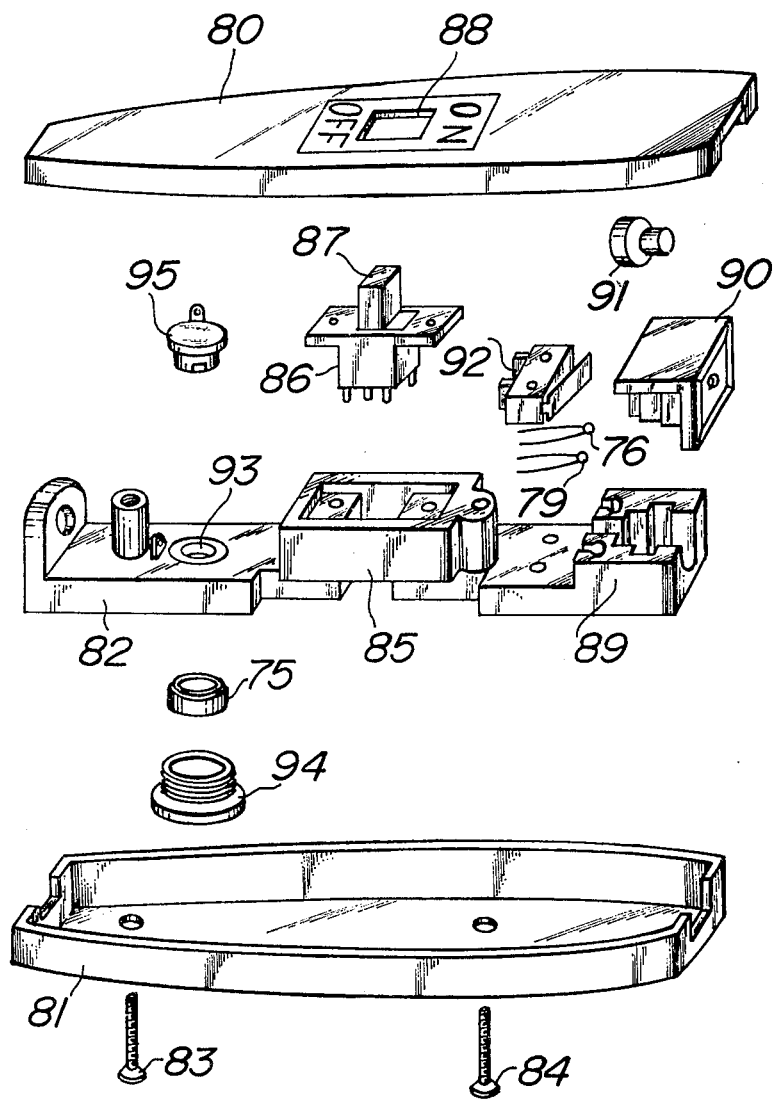

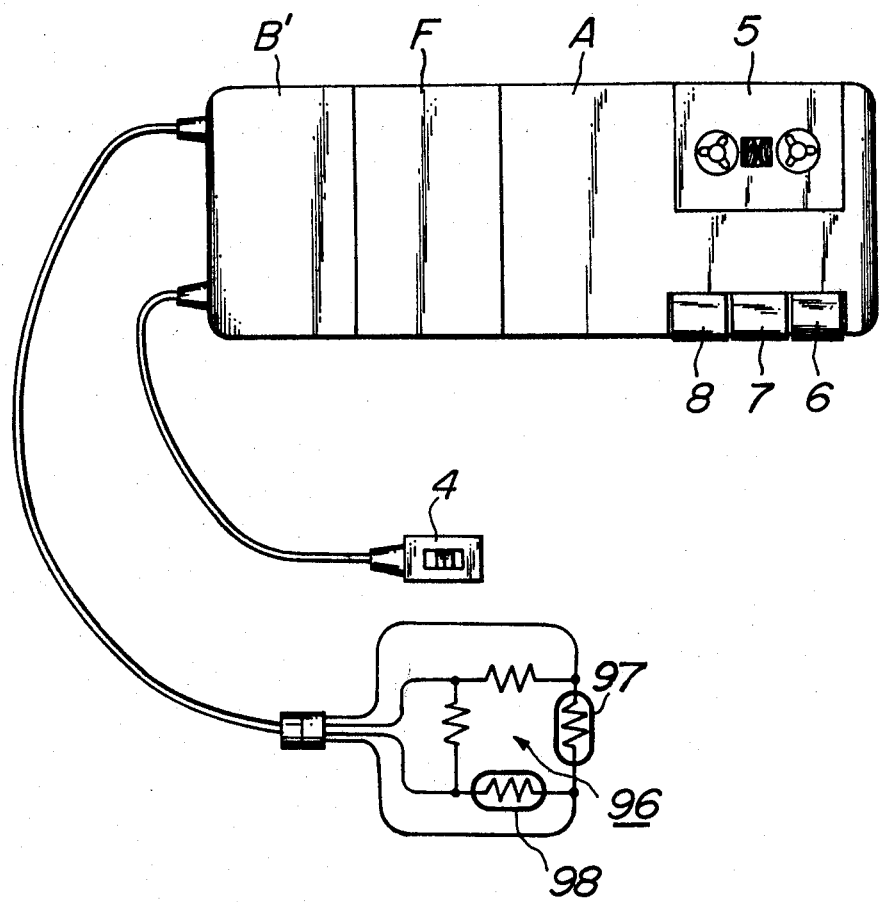
FIG_14

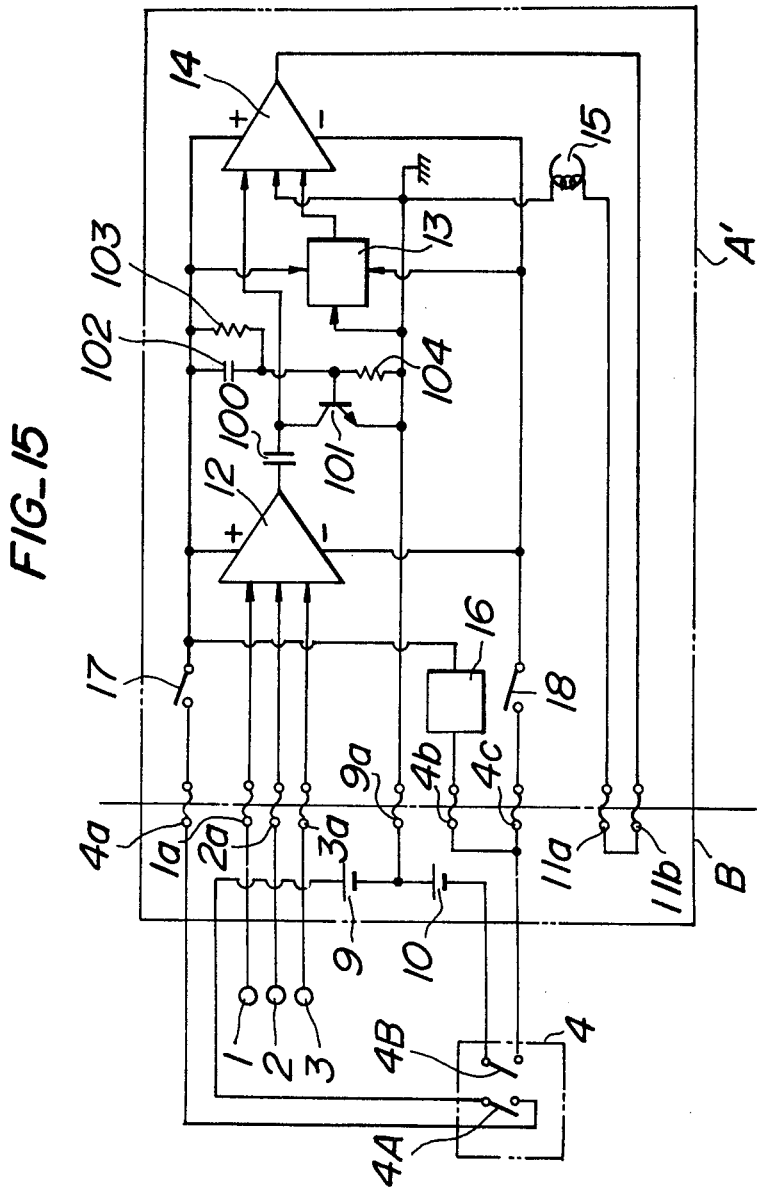
FIG_15

VITAL PHENOMENON RECORDING AND/OR REPRODUCING DEVICE

This application is a continuation application of Ser. No. 374,955; filed June 29, 1973, now abandoned.

The present invention relates to a vital phenomenon recording and/or reproducing device which may be used as an electrocardiograph, an electromyograph, an electroencephalograph, etc. and more particularly a device for recording magnetically bio-electric potential signals produced by vital phenomena on a magnetic tape and/or reproducing the signals recorded on the tape.

In the device of the kind mentioned above, in general, the bio-electric potential signal is detected by electrodes adhered to a body of a patient, so that the device and the patient are electrically connected to each other. Therefore it is necessary to protect the patient from an electric shock. A safety device for protecting the patient against the electric shock is always provided in the device for handling electrically the vital phenomena. However, in case the device is energized by an AC supply, it is impossible to protect completely the patient under any condition. Particularly when a size of the device becomes smaller, a possibility of short-circuit will increase and a fear that the patient is subjected to the electric shock will be greater.

For example, in an electrocardiography it is necessary to obtain an electrocardiogram at a fit of the patient. To this end it has been proposed that a vital phenomenon at a fit is recorded on a magnetic tape by a portable type magnetic tape recorder carried with the patient and after that said magnetic tape is loaded on a magnetic reproducing device installed at a hospital or a laboratory so as to read-out the recorded signal and an electrocardiogram is formed by, for example, an XY recorder. An electrocardiographer checks the electrocardiogram thus formed and can diagnose various diseases about a heart of the patient. In such an electrocardiograph, since the tape recorder operates usually at a low voltage and a small current, although the electrodes connected to the tape recorder are adhered to suitable portions of a body, it is considered that a fear of electric shock can be avoided completely. However, in such a system the recording and reproducing are effected by different devices, so that they must be matched accurately. If the matching is not correct, amplitudes and waveforms of the electrocardiogram differ from actual ones and it is impossible to effect a correct diagnosis. In fact it is quite difficult to match completely the recording device with the reproducing device and there is a serious drawback that a cost of the device becomes very high.

In order to avoid such drawbacks, it is easily conceived to effect the recording and reproducing by the same device. But in this case there will be trouble about the electric shock. That is to say, in case of using an electrocardiograph, a patient visits a doctor and the doctor adheres three electrodes onto given portions of the body. This operation of adhesion of the electrodes is quite critical and it is necessary to check whether or not a correct electrocardiogram can be obtained after the electrodes have been adhered to the body. To this end the doctor operates the magnetic tape recorder so as to record a bio-electric potential on a magnetic tape and then the recorded signal is reproduced. The reproduced signal is supplied to a recorder so as to draw an electrocardiogram. The doctor can determine the condition of adhesion of the electrodes to the body by checking the electrocardiogram thus formed. In such a case, the patient is connected through the electrodes and the magnetic tape recorder which operates with a battery to the recorder which is energized with an AC supply. As a result there is a danger that the patient will be subjected to the electric shock. In this case such a danger may be avoided by providing a plug and a jack for connecting the electrodes to the magnetic tape recorder and disconnecting the electrodes from the magnetic tape recorder. When the tape recorder is operated in a reproduction mode, said plug connected to the electrodes are disconnected from the jack so as to disconnect the patient from the tape recorder. However, as long as the connection and disconnection must be carried out by a human being, it cannot be always warranted that the plug of the electrodes is drawn out in the reproduction mode, so that the electric shock cannot be always avoided. Moreover, the vital potential signal has an ultra-low frequency and such a signal of ultra-low frequency cannot be magnetically recorded as in the case of recording an audio signal, but must be recorded with pulse width modulation or frequency modulation method. Therefore, a reproduced signal must be demodulated. In this case if a demodulator is provided separately from the tape recorder and an output from a head amplifier is supplied to the demodulator through a connecting wire of a relatively long length, there will be a drawback that the head output is affected by ambient noise to a great extent. In order to avoid such a disadvantage the demodulator may be fitted in the tape recorder, but in this case the device becomes larger and is inconvenient for carrying.

In the electrocardiography an amplitude of the bio-electrical potential of a heart is about 0.1 to 2 mV, when the potential is derived indirectly from a skin surface. On the other hand, in the electroencephalography, an amplitude of the bio-electrical potential of a brain is about 10 to 250 $\mu$V, when the potential is indirectly derived from a skin of a head. In this manner the amplitudes of the input voltages greatly differ from each other. Thus in fact it is impossible to record these signals by means of the same circuit. However, it is quite expensive to prepare independent recording devices for the electrocardiography, electromyography, electroencephalography, etc. Therefore, it is desirable to provide a single device which can be used for the various applications. For example, it is desired to provide a pre-amplifier which may be selectively used for amplifying a bio-electric signal of a small amplitude. Moreover, it is quite advantageous to arrange a battery checking circuit for checking a weariness of a battery, a generator for producing calibration voltage pulses having a constant amplitude and/or a constant interval, an automatic starting circuit, etc. In some applications, it is desired to provide a transmitter so as to transmit a reproduced signal in a wireless mode. However, if these circuits are installed in the magnetic recording and/or reproducing device, the device becomes large, expensive and complicated. Particularly the large device is inconvenient for carrying and handling.

As described above, since the bio-electrical potential has an ultra-low frequency, it cannot be recorded on the magnetic tape in the same manner as recording an audio signal and thus the pulse width modulation or frequency modulation must be utilized. When the ultra-low frequency signal is recorded with such a modulation method, a reproduced output supplied from a magnetic head during the reproduction is of substantially pulsatory. In the vital phenomenon recording device, the magnetic heads have different characteristics and as the result the head amplifier output fluctuates for each device. Moreover, if peak values of the head amplifier output differ from each device, a waveform converting operation at the succeeding demodulator becomes unstable and accurate records of vital phenomena could not be obtained. Therefore, it is quite preferable to provide an automatic gain control circuit for controlling a gain of the head amplifier.

As mentioned above a patient visits a doctor and the doctor adheres electrodes to the body of the patient. At this moment it is possible to check whether or not the electrodes are correctly adhered to the body. However, after that the connection between the electrodes and the body might be deteriorated or even broken in the worst case. In such a case correct recording cannot be achieved. Moreover, in the recording process, the circuit might work imperfectly, and also in this case a correct recording could not be effected. Therefore it is quite convenient for the patient that a monitor device is provided in the recording device and the patient can determine whether or not the recording device works correctly in the reocrding process.

In the magnetic recording device the bioelectrical potential having ultra-low frequency must be amplified and thus the head amplifier must have a frequency characteristic which has a flat portion over a frequency range of about 0.1 to 1,000 Hz. To an output of such an amplifier is connected a capacitor for cutting a DC component. Since this capacitor should pass the ultra-low frequency signal, it is required to use a large size capacitor. When use is made of such a large size capacitor, the device does not operate immediately after the device is switched on, but the device starts to work satisfactorily only after a quite long time period, in general several seconds has been elapsed. In order to start the device immediately after the device is actuated, usually an instomatic circuit is provided in the vital phenomenon recording device.

It is a primary object of the present invention to provide a vital phenomenon recording and/or reproducing device which can protect completely a user or a patient against an electric shock under any condition.

It is another object of the invention to provide a vital phenomenon magnetic recording and/or reproducing device, wherein a magnetic tape driving mechanism and a magnetic head can be used commonly for recording and reproducing so as to obtain accurate electrocardiogram, electromyogram, electroencephalogram, etc.

It is another object of the invention to provide a vital phenomenon recording and/or reproducing device, in which a preamplifier, a battery checking circuit, a calibration voltage producing circuit, a transmitter, an automatic starting circuit, a voltage source for a bridge circuit of a wire resistance strain gauge, etc. are prepared as attachments and one or more of these attachments can be selectively connected to a main unit of the device.

It is further object of the invention to provide a vital phenomenon recording and/or reproducing device which comprises an automatic gain control circuit for adjusting an amplitude of the head amplifier output, so that an accurate vital phenomenon signal can be reproduced.

It is another object of the invention to provide a vital phenomenon recording and/or reproducing device which comprises a monitor device for checking an operation of the device during the recording process.

It is still another object of the invention to provide a vital phenomenon recording and/or reproducing device which comprises an instomatic circuit for starting positively the device in the recording process immediately after the device is actuated.

According to a basic aspect of the present invention a vital phenomenon recording and/or reproducing device comprises a main unit having at least a magnetic tape driving mechanism and a magetic head, a recording attachment capable of being connected to said main unit mechanically and electrically in a recording process and having at least one measuring electrode connected thereto, and a reproducing attachment capable of being connected to said main unit mechanically and electrically in a reproducing process and also being connected to a recorder, whereby either one of said recording and reproducing attachments is coupled selectively to said main unit so as not to effect the reproducing operation during the recording operation.

According to the present invention, in the recording operation a body of a patient is electrically connected to the recording attachment and the main unit through the measuring electrodes. However, the recording attachment and the main unit are energized with a battery of low voltage which is harmless for the patient. In the reproducing process, the reproducing attachment is connected to the main unit instead of the recording attachment, so that even if the reproducing attachment is connected to the recorder which is operated by an AC source, there is no danger of electric shock, because the patient is completely disconnected from the AC source.

According to further aspect of the invention the vital phenomenon recording and/or reproducing device comprises as indispensable components a main unit including at least a magnetic tape driving mechanism and a magnetic head, a recording attachment capable of being connected to said main unit mechanically and electrically in a recording mode and including a battery, to said recording attachment being connected a detector, and a reproducing attachment capable of being connected to said main unit mechanically and electrically in a reproducing mode and also being connected to a recorder; and further comprises as arbitrary components attachments including a pre-amplifier, a battery checking circuit, a calibration voltage producing circuit, a transmitter, an automatic starting circuit, a battery for a bridge circuit of a wire resistance strain gauge, etc. or suitable combinations thereof, whereby said attachments of the arbitrary components are capable of being connected mechanically and electrically between said main unit and said recording attachment or between said main unit and said reproducing attachment in a detachable manner.

Now the present invention will be explained in greater detail with reference to accompanied drawings; in which:

FIG. 1 is a perspective view of an embodiment of the vital phenomenon recording and/or reproducing device according to the invention in a recording mode;

FIG. 2 is a circuit diagram of the device shown in FIG. 1;

FIG. 3 is a plan view of the device in a reproducing mode;

FIG. 4 is a circuit diagram of the device shown in FIG. 3;

FIG. 5 is a plan view of another embodiment of the device according to the invention in a recording mode;

FIG. 6 is a circuit diagram of the device shown in FIG. 5;

FIG. 7 is a circuit diagram of another embodiment of the device according to the invention in a reproducing mode, which comprises a reproducing attachment including an automatic gain control circuit;

FIG. 8, is a plan view of another emboidment of the device according to the invention in a recording mode, in which an attachment for producing calibration voltage pulses having given amplitude and repetition frequency is coupled between a main unit and a recording unit;

FIG. 9 is a circuit diagram of the device shown in FIG. 8;

FIG. 10 shows a plan view of the device according to the invention in a recording mode, which device comprises an attachment for checking a battery and producing calibration voltage pulses;

FIG. 11 is a circuit diagram of the device shown in FIG. 10;

FIG. 12 is a circuit diagram of another embodiment of the device according to the invention in a recording mode, in which calibration voltage pulses having a given amplitude can be manually produced by depressing a button provided on a remote switch;

FIG. 13 is a perspective view of the remote switch shown in FIG. 12 in a decomposite form;

FIG. 14 is a plan view illustrating another embodiment of the device according to the invention, which device comprises an attachment accomodating a battery for energizing a bridge circuit of a wire resistance strain gauge; and FIG. 15 is a circuit diagram of another embodiment of the device according to the invention in a recording mode, in which device an instomatic circuit is included in a main unit.

A first embodiment of the vital phenomenon recording and/or reproducing device according to the invention, which can be used as an electrocardiograph will be explained with reference to FIGS. 1 to 4. FIG. 1 shows the device in a recording mode. In the recording process, to a main unit A comprising at least a tape driving mechanism and a magnetic head is connected mechanically and electrically a recording attachment B including a battery for energizing said driving mechanism and various circuits. To the recording attachment B there are connected three measuring electrodes 1, 2 and 3 and a remote switch 4. The main unit A further comprises a receptacle for receiving a tape cassette 5 and operating members 6, 7 and 8. In the present embodiment, the operating members consist of a play button 6, a stop button 7 and a rewind button 8.

FIG. 2 shows internal circuit portions of the main unit A and the recording attachment B. As shown in a right hand portion of FIG. 2, there are arranged batteries 9 and 10 in the recording attachment B. The connection between the main unit A and the recording attachment B is electrical as well as mechanical. As a coupling mechanism for this purpose use may be made of a bayonet mount type coupling mechanism, a pin type coupling mechanism or any other coupling mechanism. In the recording attachment B, there are provided nine connecting contacts, i.e., contacts 1a, 2a and 3a connected to the measuring electrodes 1, 2 and 3, respectively, contacts 4a, 4b and 4c connected to two contacts 4A and 4B of the remote switch 4, a contact 9a connected to a junction point of the batteries 9 and 10, and contacts 11a and 11b connected to each other. The main unit A comprises nine contacts each of which is capable of being connected to each of corresponding nine contacts of the recording attachment B. The main unit A further comprises a balanced D.C. amplifier 12 having input terminals connected to the measuring electrodes 1, 2 and 3 via the contacts 1a, 2a and 3a, respectively, an oscillator 13 connected across the contacts 4a and 4c, a modulator and head driving circuit 14, a magnetic head 15 and a motor and motor speed control circuit 16 inserted between the contacts 4a and 4b. In FIG. 2, there is not shown the tape driving mechanism and the operating members, but there are shown switches 17 and 18 which are actuated by the operating members. Since the remote switch 4 is provided, the switches 17 and 18 are not always necessary, but if the remote switch 4 is erroneously actuated, the batteries 9 and 10 are wasted and moreover the electric circuit is made operated. In order to avoid such disadvantage, in the present embodiment there are provided the switches 17 and 18 interlocked with the operating members. In this case the switches 17 and 18 are opened under the rest condition and when the play button 6 is actuated, both switches 17 and 18 are closed. When the rewind button 8 is depressed, only the switch 17 is closed and only the motor and motor speed control circuit 16 is energized, but the remaining circuits are not energized.

In case of recording a vital phenomenon, a bioelectrical potential is detected by the electrodes 1, 2 and 3 and the detected signal is suitably amplified and then is recorded. As described above, the bio-electrical signal has an ultra-low frequency, so that when such a signal of the ultra-low frequency is recorded on a magnetic tape an ordinal recording method for recording an audio signal cannot be utilized. Therefore, it is necessary to record the bio-electrical signal on the magnetic tape with the pulse-width modulation method, frequency modulation method, etc. In the electrocardiograph of the present embodiment, use is made of the pulse-width modulation method. A bio-electrical potential signal detected by the electrodes 1, 2 and 3 has an amplitude of about 1 mV and a frequency range of about 0.1 to 200 Hz. This detected signal is amplified by the D.C. amplifier 12. The amplified signal is supplied to one input terminal of the modulator 14. To the other input terminal of the modulator 14 is supplied a carrier signal of square wave having a repetition frequency of, for example, 400 KHz from the oscillator 13. A pulse width, i.e., a duty cycle of the square wave is modulated by the amplified bio-electrical signal. Then the modulated carrier is suitably amplified and the amplified signal is supplied to the magnetic head 15 and is recorded on the magnetic tape as positive and negative magnetizations beyond the magnetic saturation.

FIG. 3 illustrates the device in a reproducing mode. In this mode, the recording attachment B is detached from the main unit A and a reproducing attachment C is coupled with the main unit A. To the reproducing attachment C is connected a connecting wire 20, the other end of which wire is connected to a demodulator unit 19. The demodulator unit 19 is connected to a recorder 21 with a writing pen. The demodulator unit 19 and the recorder 21 are energized with an A.C.

supply.

FIG. 4 shows an internal construction of the reproducing unit C. In the reproducing unit C, there is provided a head amplifier 22 which amplifies a signal reproduced by the magnetic head 15. As explained above in the present embodiment use is made of the pulse-width modulation method, so that the head output is of a pulsatory signal. The amplified signal from the head amplifier 22 is supplied to a demodulator 23 in the demodulator unit 19 through the connecting wire 20. The demodulator 23 demodulates the pulsatory signal to produce the original bio-electrical signal of an ultra-low frequency. The bio-electrical signal thus reproduced is supplied to the recorder 21 and the recorder 21 draws an electrocardiogram.

In the present embodiment there is provided a rectifying circuit 24 in the demodulator unit 19 and D.C. voltage produced by this rectifying circuit 24 is supplied to the main unit A through the connecting wire 20 so as to energize the motor and motor speed control circuit 16 in the reproducing mode. In the reproducing mode, the switch 17 must be closed, but the switch 18 may or may not be closed, because a contact connected to the switch 18 is floating.

As described above, according to the invention, since in the recording mode the recording attachment B is connected to the main unit A and the device is energized by the batteries 9 and 10 which are absolutely safe for the patient and in the reproducing mode since the recording attachment B is disconnected from the main unit A and the reproducing attachment C is connected to the main unit A, the patient can be completely protected against the electric shock. Moreover, in the reproducing mode the head amplifier 22 can be arranged near the magnetic head 15, so that the head output is hardly affected by the surrounding noise and an accurate electrocardiogram can be obtained. Further since the same tape driving mechanism and the same magnetic head 15 can be used both in the recording and reproducing modes, a more accurate electrocardiogram can be formed. In the reproducing mode since the amplifier 12, the oscillator 13, the modulator 14, etc. are maintained to be de-energized, there is not a fear that noise due to these circuits is included in the head output.

As explained above, when the vital phenomenon of a heart of a patient is to be recorded, he must visit a doctor and the doctor adheres the measuring electrodes to given parts of the body of the patient. Then the doctor checks whether or not the device works satisfactorily and also whether or not the electrodes are correctly adhered to the body. However the connection between the electrodes and the body might be deteriorated after the patient leaves the doctor. Then it is impossible to record the bio-electrical signal in the correct manner. In order to avoid such a failure of recording, a next embodiment according to the invention comprises a monitor device for checking the recording signal.

FIG. 5 shows the construction of such an embodiment in the recording mode and FIG. 6 illustrates the internal construction thereof. As can be seen from FIGS. 5 and 6, in the recording mode, a recording attachment B is coupled with a main unit A'. The construction of the recording attachment B is exactly the same as that of the recording attachment B shown in FIG. 2. But the construction of the main unit A' is slightly different from that of the main unit A shown in FIG. 2. That is, in the present embodiment, to the output of the modulator 14 is connected a jack 25 in parallel with the magnetic head 15 and an earphone plug 26 connected to an earphone 27 can be inserted into the jack 25. Thus a part of the output signal from the modulator 14 is supplied to the earphone 27 having a sufficiently higher impedance than that of the magnetic head 15 through the jack 25 and the plug 26. This output signal from the modulator 14 is the square wave carrier signal of 400 Hz modulated by the ultra-low frequency signal of 0.1 to 100 Hz and thus is audible by the earphone 27. In this case when the device works correctly, one can hear the signal of 400 Hz (this is heard by an ear as a continuous signal having a constant strength) modulated by the vital phenomenon signal of an ultra-low frequency. On the contrary, when the electrodes 1, 2 and 3 are not correctly adhered to the body, the amplifier 12, the oscillator 13, the modulator 14, etc. do not operate correctly, the batteries 9 and 10 are too worn out, or the main unit A' and the recording attachment B is not coupled correctly, one cannot hear a regular sound. In this manner one can determine whether or not the recording is effected perfectly by checking sound produced by the earphone 27. When the correct recording is not carried out, no sound is heard form the earphone 27 or one can hear different sound than that is correctly modulated by the vital phenomenon signal.

FIG. 7 shows another embodiment of the device according to the invention in a reproducing mode. A main unit A, a modulator unit 19 and a recorder 21 are entirely the same as those shown in FIG. 4. A reproducing attachment C' of the present embodiment comprises a head amplifier 22 in the form of a differential amplifier having a positive input terminal connected to the magnetic head 15. A part of the output signal from the amplifier 22 is extracted by means of a diode 28 and a resistor 29. The output signal from the head amplifier 22 is positive and negative pulsatory signal, so that positive pulses are passed through the diode 28 and supplied to an integrator 30 including a differential amplifier and a feedback capacitor. The integrator 30 produces at its output a negative signal. The output of the integrator 30 is connected to a base of a transistor 31 having an emitter connected to the earth through a potentiometer 32 and a collector connected to a negative potential. A tap of the potentiometer 32 is connected to a gate of a field effect transistor 33 having a drain connected to a negative input terminal of the head amplifier 22 and a source connected to the earth. The output terminal of the head amplifier 22 is connected to the negative input terminal of the head amplifier 22 through a resistor 34. The diode 28, the resistor 29, the integrator 30, the transistor 31, the potentiometer 32, the field effect transistor 33 and the resistor 34 constitute an automatic gain control (AGC) circuit for the head amplifier 22 and by means of this AGC circuit the amplifier 22 can produce output pulses having substantially the constant peak values.

When the reproduced signal from the magnetic head 15 increases, the output signal from the head amplifier 22 also increases. The positive portion of this increased pulse signal is supplied to the integrator 30, and thus the output from the integrator 30 also increases in a negative sense. Therefore the transistor 31 is operated into a more conductive state and the voltage at the tap of the potentiomerer 32 increases in a negative sense. Thus the field effect transistor 33 is caused into the non-conductive condition and its drain-source resistance $R_E$ increases apparently. Now if a resistance value of the resistor 34 is denoted by $R_f$, a gain of the head amplifier 22 can be expressed by $R_f/R_E$. Therefore, when the resistance $R_E$ increases, the gain of the head amplifier 22 becomes smaller and thus amplitudes of its output pulses become smaller. On the contrary when the output from the head amplifier 22 becomes decreased, the AGC circuit operates in the opposite manner to that described above and the resistance $R_E$ becomes smaller and thus the gain of the head amplifier 22 increases. In this manner, the gain of the head amplifier 22 is automatically controlled and the output pulses having adjusted peak value can be obtained. Therefore, the demodulating operation of the demodulator 23 is made stable and an accurate electrocardiogram can be formed by the recorder 21.

For example, in the electrocardiograph, it is desired to record calibration voltage pulses having an amplitude of for example 1 mV so as to supervise the operational condition of the amplifying circuit and to determine the amplitude of the bio-electrical potential of a heart on the basis of a height and a width of the calibration voltage pulses. Moreover, by means of the calibration voltage pulses it is possible to adjust a gain of the recorder for forming the electrocardiogram. Moreover, when use is made of the calibration pulses having a constant repetition frequency, it is possible to know the pulse frequency.

When the recording device operating as the electrocardiograph according to the invention is used, a patient carries always the device and when he is subjected to a fit, he actuates the device and the bio-electrical potential signal may be recorded on a magnetic tape. However, it is very difficult for the patient to actuate a calibration voltage producing circuit as well as the recording device when he is attacked by a fit. Thus it is quite convenient to produce automatically the calibration voltage pulses for a given time period each time the recording device is switched on.

According to the invention, such a calibration voltage producing circuit can be provided as a calibration voltage pulse producing attachment which can be connected between the main unit A and the recording attachment B.

FIG. 8 illustrates such an embodiment and FIG. 9 shows the internal construction thereof. As shown in FIGS. 8 and 9, the main unit A and the recording attachment B are the same as those shown in FIG. 2. In FIG. 9, the calibration voltage pulse producing attachment D comprises a calibration voltage pulse producing circuit composed of a delay circuit, a switching circuit, a monostable multivibrator and a constant current supply source. The delay circuit is constructed as a Schmit circuit comprising mainly a resistor 35, a capacitor 36 and transistors 37 and 38. The switching circuit is consisted of a transistor 39 and a relay 40 which operates relay switches 41, 42 and 43. The mono-stable multivibrator is constructed mainly by a transistors 44 and 45, resistors 46 and 47 and capacitors 48 and 49. By chosing suitable values of the resistors 46 and 47 and the capacitors 48 and 49, the calibration voltage pulse having a given pulse width and a given pulse interval can be obtained. An output from the mono-stable multivibrator is applied to a base of a transistor 50 serving as the constant current supply source. In series with the transistor 50 are connected a field effect transistor 51, a variable resistor 52 and a fixed resistor 53.

The calibration voltage pulse producing circuit according to the present invention operates as follows. When the remote switch 4 is actuated and its contacts 4A and 4B are closed, the amplifier 12, the oscillator 13, the modulator 14 and the motor and motor speed control circuit 16 in the main unit A are energized and the device is prepared to record the bio-electrical signal detected by the measuring electrodes 1, 2 and 3 connected to the recording attachment B. At the same time the transistor 38 in the delay circuit is made conductive, whereas the transistor 37 is kept non-conductive. Thus the transistor 39 in the switching circuit is made conductive and the relay 40 is energized by the batteries 9 and 10 through the contacts 4A and 4B. Before the relay 40 is energized, the switches 41, 42 and 43 are in positions shown in FIG. 9 and when the relay 40 is energized, the switches 41, 42 and 43 are changed into positions opposite to those shown in the drawing. By changing the switch 41, the mono-stable multivibrator is energized and at the same time by changing the switches 42 and 43, the measuring electrodes 1 and 3 are disconnected from the amplifier 12. Then the mono-stable multivibrator produces a pulse series having a given pulse width and a given pulse interval. This pulse series is applied to the base of the transistor 50 serving as the constant current source and the transistor 50 is repeatedly made conductive. In this case a current flowing through the transistor 50 is kept constant in regardless to a fluctuation of a voltage of the batteries 9 and 10. This current also passes through the field effect transistor 51, the variable resistor 52 and the fixed resistor 53. By means of the variable resistor 52 the value of said current can be adjusted. For example, when use is made of the field effect transistor 51 of junction type, it is preferable to adjust the value of the variable resistor 32 in such a manner that the current is kept to a level of 0.25 to 0.3 mA, at which level the current is hardly affected by temperature variation. The resistor 53 is selected to such a value that there is produced a calibration voltage pulse of 1 mV across the resistor 53. In this manner, there are produced across the resistor 53 a calibration pulse series having a pulse width of 100 ms, a pulse interval of 400 ms and an amplitude of 1 mV. The calibration voltage pulse series thus produced is then applied to the amplifier 12 through the switch 42. The other input terminals of the amplifier 12 are connected to the earth. The calibration voltage pulse series is recorded on the magnetic tape by means of the amplifier 12, the modulator 14 and the magnetic head 15.

The calibration voltage pulses are produced as long as the relay 40 is energized. After a delay time of a few seconds determined by the values of the resistor 35 and the capacitor 36 has been elapsed, the transistor 17 changes to a conductive state and thus the transistor 18 is made cut-off. Therefore the transistor 39 is also made non-conductive and the relay 40 is de-energized. Thus the switches 41, 42 and 43 are returned to the initial positions shown in FIG. 9 and the mono-stable multivibrator is de-energized. In this manner the generation of the calibration pulse series is stopped. At the same time the measuring electrodes 1, 2 and 3 are connected to the amplifier 12. In this manner the bio-electric signal of a heart can be recorded on the magnetic tape by means of the amplifier 12, the modulator 14 and the magnetic head 15. The transistor 37 is kept conductive until the remote switch 4 is switched off.

FIG. 10 shows further embodiment of the vital phenomenon recording and/or reproducing device according to the invention in a recording mode. In the present embodiment between a main unit A and a recording attachment B there is coupled an attachment E including a battery checking circuit and a calibration voltage pulse producing circuit. The calibration voltage pulse producing circuit of this embodiment is substantially the same as that shown in FIG. 9, but in the present embodiment the calibration voltage producing circuit is not automatically started by actuating the remote switch 4. As shown in FIG. 10, the attachment E comprises a battery checking button 54, a calibration voltage producing button 55 and a pair of battery checking meters 56 and 57, in this embodiment voltmeters.

FIG. 11 illustrates an internal connection of the recording device of this embodiment. On either sides of the attachment E, there are provided nine contacts for connecting the attachment E to the main unit A and the recording attachment B. Two contacts connected to the contacts 4a and 4c of the recording attachment B are connected to arms of switches 58 and 59, respectively. One of contact of the switch 58 is connected to one of contacts of the switch 59 through a series circuit of resistors 60 and 61, a junction point of which resistors is connected to the contact 9a connected to the junction point of the batteries 9 and 10. The contact 9a is connected to the earth. The voltmeters 56 and 57 are connected in parallel with the resistors 60 and 61, respectively. The other contact of the switch 58 is connected to a contact 62 and the other contact of the switch 59 is connected to contacts 63 and 64.

The other contact of the switch 58 is connected to a contact of a switch 65 and an arm of this switch 65 is connected to a calibration voltage pulse producing circuit 66. The circuit 66 is further connected to the earth. An output terminal of the circuit 66 is connected to one contact of a switch 67, the other contact of which is connected to the contact 1a coupled to the measuring electrode 1. A switching arm of the switch 67 is connected to a contact 68. The contact 2a connected the electrode 2 is directly connected to a contact 69 and the contact 3a connected to the measuring electrode 3 is connected to one contact of a switch 70, the other contact of which is connected to the earth. A switching arm of this switch 70 is connected to a contact 71. The contact 9a connected to the junction point of the batteries 9 and 10 is directly connected to a contact 72. Further contacts 73 and 74 are connected to each other.

The switches 58 and 59 are actuated by the battery checking button 54 and when the button 54 is depressed, the switching arms of these switches 58 and 59 are changed to positions opposite to those shown in FIG. 11. The switches 65, 67 and 70 are operated by the calibration voltage producing button 55 in such a manner that when the button 55 is depressed, the switching arms of these switches 65, 67 and 70 are changed to positions opposite to those shown in FIG. 11. Thus, FIG. 11 illustrates a condition in which the batteries 54 and 55 are not depressed and in this condition a bio-electrical signal can be recorded by actuating the remote switch 4. When the battery checking button 54 is depressed, the switching arms of the switches 58 and 59 are changed. Then a current passes from the positive terminal of the battery 9 through the contact 4A of the remote switch 4, the switch 58, the resistor 60 and the contact 9a to the negative terminal of the battery 9. At the same time, a current passes from the positive terminal of the battery 10 through the contact 9a the resistor 61, the switch 59, the contact 4c and the contact 4B of the remote switch 4. Thus voltage drops appear across the resistors 60 and 61, respectively. These voltage drops are measured by the voltmeters 56 and 57, respectively. In this matter the weariness of the batteries 9 and 10 can be checked separately. In this case values of the resistors 60 and 61 are selected in such a manner that the current passing through these resistors 60 and 61 is equal to a current through the device when the device is actually operated. Therefore the voltage values read-out by the voltmeters 56 and 57 represent the voltages which are actually applied to the device in an operating condition.

When the calibration voltage producing button 55 is depressed, the switching arms of the switches 65, 67 and 70 are changed to positions opposite to those shown in FIG. 11. Then the calibration voltage pulse producing circuit 66 is energized and produces a calibration voltage pulse series which is supplied to the amplifier 12 of the main unit A through the switches 58 and 70 and recorded on the magnetic tape by means of the magnetic head 15. The calibration voltage pulse generating circuit 66 is exactly the same as that shown in FIG. 9 and comprises a mono-stable multivibrator and a constant current supply source.

In the present embodiment the reproduction of the recorded bio-electrical signal may be effected by coupling the reproducing attachment C with the main unit A just like as shown in FIG. 3.

In the above embodiments shown in FIGS. 9 and 11, the calibration voltage pulse producing circuit generates a calibration voltage pulse series having the given amplitude, pulse width and pulse interval. Such a calibration pulse series is quite useful to analyze precisely the electrocardiogram, electromyogram, electroencephalogram, etc. But in many cases it is often sufficient to produce calibration voltage pulses which have only a given amplitude.

FIG. 12 shows further embodiment of the device according to the invention in a reocrding mode, in which calibration voltage pulses having a given amplitude can be manually produced. In FIG. 12, the main unit A and recording attachment B are exactly the same as those shown in FIG. 2. In the present embodiment in a housing of a remote switch 4', there is provided a calibration voltage pulse producing circuit. That is, a battery 75, resistors 76 and 77 and three contacts 4A, 4B and 4C are arranged in the housing of the remote switch 4'. As shown in FIG. 12, the measuring electrode 1 is connected to the contact 1a through the resistor 77 and a series circuit of the battery 75, the contact 4C and the resistor 76 is connected in parallel with the resistor 77. Thus when the contacts 4A and 4B of the remote switch 4' are closed, the device can record the bio-electrical signal detected by the electrodes 1, 2 and 3 on the magnetic tape. When the contact 4C is manually closed, a current passes from the positive terminal of the battery 75 through the contact 4C and the resistors 76 and 77, so that a voltage drop appears across the resistor 77 and is applied to the amplifier 12 in the main unit A through the contact 1a. By actuating the contact 4C in an intermittent manner, said voltage drop is produced as a pulsatory signal which can be used as the calibration voltage pulses. Values of the resistors 76 and 77 are so selected that the voltage drop having a given amplitude of, for example 1 mV appears across the resistor 77.

FIG. 13 illustrates an embodiment of the remote switch 4' shown in FIG. 12. The housing of the remote switch 4' is consisted of an upper casing 80, a lower casing 81 and an intermediate frame 82. These casings and frame may be composed by means of a pair of screws 83 and 84. At a middle of the intermediate frame 83, there is formed a receptacle 85 for receiving a slide switch 86, an operating knob of which is projected from an opening 88 formed in the upper casing 80. The slide switch 86 comprises the contacts 4A and 4B shown in FIG. 12. At a right hand end of the frame 82, there is formed a receptacle 89 for accommodating a block 90 for holding a button 91, by means of which button 91 a micro switch 92 including the contact 4C shown in FIG. 12 can be actuated. Said micro switch 92 is also secured to the intermediate frame 82. In said receptacle 89, there are also formed portions for holding the resistors 76 and 77. At a left side of the intermediate frame 82, there is formed a hole 93 for accommodating the battery 75, in the present embodiment a mercury battery. The battery 75 is fixed in position by means of a cap 94 having a screw and a cap 95 having terminals. In FIG. 13, the connection for the elements is not shown, but the elements are connected as shown in FIG. 12. On a side surface of the block 90 an indication of "1 mV" is provided and a user can know that the calibration voltage of 1 mV is produced by pushing the button 91.

FIG. 14 illustrates another embodiment of the device according to the invention in a recording mode, which may record a bio-electrical signal produced by a motion of a vital body. In the present embodiment a recording attachment B' is connected to the main unit A with interposing an attachment F. To the recording attachment B' are connected a remote switch 4 and a bridge circuit of a wire resistance strain gauge 96 including wire resistances 97 and 98.

In the attachment F, there is arranged a battery for energizing the bridge circuit 96.

As already mentioned above, in general the bio-electrical potential signal has an ultra-low frequency and the amplifier for amplifying such an ultra-low frequency signal must have a flat frequency response over a frequency band from about 0.1 to about 1,000 Hz. To an output of such an amplifier is connected a capacitor for cutting a d.c. component. Since this capacitor must pass the ultra-low frequency signal, its capacitance value should be large. When use is made of such a large capacitor, the device does not operate immediately after the device is switched on, but it starts to work stably only after a considerable long time period, usually several seconds has been elapsed. In order to avoid such a long vacant time, there is usually provided an instomatic circuit in a vital phenomenon treating device.

FIG. 15 shows an embodiment of a main unit A' comprising an instomatic circuit which has a simple construction, but operates in a very stable manner. As shown in FIG. 15, the main unit A' comprises an amplifier 12, an oscillator 13, a modulator 14, a magnetic head 15 and a motor and motor speed control circuit 16. The connection of these components is substantially the same as that shown in FIG. 2. An output of the amplifier 12 is connected to an input of the modulator 14 through a capacitor 100. As explained above this capacitor 100 must have a large capacitance in order to pass the bio-electrical signal of the ultra-low frequency and thus a time constant of an RC circuit consisted of the capacitor 100 and an input impedance of the modulator 14 becomes quite long, i.e. several seconds. Therefore, when contacts 4A and 4B of a remote switch 4 are closed under the recording mode, the device cannot record the signal at once, but starts to operate satisfactorily only after several seconds.

In order to reduce such a large time constant, a transistor 101 is arranged and its emitter-collector path is connected between the capacitor 100 and an earth conductor connected to a contact 9a. Between a base of the transistor 101 and a positive conductor connected to a contact 4a is inserted a parallel circuit of a capacitor 102 and a resistor 103 and between the base of the transistor 101 and the earth conductor is inserted a resistor 104. In the recording mode (in which the contacts 17 and 18 are closed), when the remote switch 4 is closed, the capacitor 102 is charged through the resistor 104. Thus a voltage drop is produced across the resistor 104 and the transistor 101 is made conductive so as to short-circuit the input of the modulator 14. Therefore the capacitor 100 is charged quickly through the emitter-collector path of the transistor 101. When the capacitor 102 is charged up, the voltage drop across the resistor disappears and the transistor 101 is made non-conductive. Since an impedance of the emitter-collector path of the transistor 101 in the conductive state is extremely lower than the input impedance of the modulator 14, the large capacitor 100 is quickly charged during the transistor 101 is conductive. Then the transistor 101 is made automatically cut-off and the device can work stably. In this manner, the device can record stably the bio-electrical signal immediately after the remote switch 4 is actuated.

The present invention is not limited to the embodiments explained so far, but may modifications may be possible. For example, in the above embodiments the play button 6, the stop button 7 and the rewind button 8 are provided in the main unit A, but if the rewinding operation is effected by other devices or use is made of an endless tape, it is possible to omit the rewind button 8. Further the main unit A may comprise an audio amplifier and an output from the modulator 14 may be supplied to the magnetic head 15 through said audio amplifier. In such a case an audio signal can be recorded on the magnetic tape, so that a patient or a doctor may record necessary informations on the tape if a microphone is connected to the main unit A or is installed in the main unit A. In the above embodiments the amplifier 12, the oscillator 13, the modulator 14 as well as the tape driving mechanism and the magnetic head 15 are arranged in the main unit A, but only the tape driving mechanism and the magnetic head 15 may be provided in the main unit A and the amplifier 12, the oscillator 13 and the modulator 14 may be installed in the recording attachment B. Further a part of the modulated signal supplied to the magnetic head 15 is derived by utilizing the jack 25 and the plug 26. The extracted signal is supplied to a demodulator through an electromagnetic coupling unit or a light coupling unit which are completely separated from the device, and the demodulated signal is supplied to a recorder or an oscillograph. As the electromagnetic coupling unit, use may be made of a transformer having completely separated primary and secondary windings. Further as the light coupling unit a combination of a light emitting diode and a photocell may be used.

The vital phenomenon recording and/or reproducing device according to the invention has many advantages which may be summarized as follows:

1. Since a patient is disconnected completely from devices which are energized by an AC supply under any condition, the patient can be always protected against an electric shock.
2. Since the device comprises only a minimum number of components indispensable for recording, the device in a recording mode becomes extremely small in size and light in weight, so that it is easy to carry and handle the device.
3. Since the main unit comprising the tape driving mechanism and the magnetic head can be used both for recording and reproducing, accurate electrocardiogram, electromyogram, electroencephalogram, etc. can be obtained.
4. Since the main unit, the recording attachment and the reproducing attachment can be commonly used for electrocardiograph, electromyograph, electroencephalograph, etc., it is not necessary to prepare many devices, so that a whole system becomes quite inexpensive.
5. Since the calibration voltage pulses having a given amplitude, a given pulse width and a given repetition frequency can be produced, accurate analysis for recorded waveforms can be effected.
6. Since the device in a recording mode is suitable to be carried with a patient, it is possible to record a bio-electrical signal at a fit of the patient, wherever the patient is.

What is claimed is:

1. An apparatus for recording and reproducing a bio-electrical signal produced by a living body comprises a main unit including
a casing having a portion for accommodating a magnetic tape and a side wall with mechanically coupling means,
a recording and reproducing magnetic head,
means for driving said magnetic tape through said magnetic head,
signal input terminals provided on said side wall of said casing for receiving said bio-electrical signal to be recorded on said magnetic tape,
an amplifier connected to said signal input terminals for amplifying said bio-electrical signal,
a modulator connected to an output of said amplifier for modulating said amplified bio-electrical signal to produce a modulated bio-electrical signal which is recorded on said magnetic tape by means of said magnetic head,
signal output terminals provided on said side wall of said casing and connected to said magnetic head to supply the modulated bio-electrical signal reproduced by said magnetic head to the external of the main unit,
power supply input terminals provided on said side wall of the casing for receiving power supply for said tape driving means, amplifier and modulator, and
an operating member provided on said casing for selectively operating said main unit in a recording mode in which said magnetic tape is driven by said tape driving means and the bio-electrical signal received by said signal input terminals is amplified and modulated and then the modulated bio-electrical signal is recorded on said travelling magnetic tape by said magnetic head and in a reproducing mode in which said magnetic tape is driven by said tape driving means and the modulated bio-electrical signal is reproduced from said travelling magnetic tape by means of said magnetic head and the reproduced signal is supplied to said signal output terminals;

a recording attachment including
a casing having a side wall with mechanically coupling means which cooperate with said mechanically coupling means of said main unit to mechanically couple said recording attachment to said main unit at their side walls,
battery means installed in said casing,
signal output terminals provided on sakd side wall of the recording attachment, said signal output terminals being connected to said signal input terminals of said main unit when said recording attachment is mechanically coupled to said main unit at their side walls,
power supply output terminals provided on said side wall of said casing of the recording attachment and connected to said battery means, said power supply output terminals being connected to said power supply input terminals of said main unit when said recording attachment is mechanically coupled to said main unit at their side walls, and
a detector for detecting said bio-electrical signal from the living body and connected to said casing of the recording attachment through an electrical conductor which is further connected to said signal output terminals of the recording attachment;

a reproducing attachment including
a casing having a side wall with mechanically coupling means which cooperate with said mechanically coupling means of the main unit to mechanically couple said reproducing attachment to said main unit at their side walls,
signal input terminals provided on said side wall of the reproducing attachment, said signal input terminals being connected to said signal output terminals of the main unit when said reproducing attachment is mechanically coupled to said main unit at their side walls,
power supply output terminals provided on said side wall of the reproducing attachment, said power supply output terminals being connected to said power supply input terminals of the main unit when said reproducing attachment is mechanically coupled to said main unit at their side walls,
an amplifier having an input connected to said signal input terminals of the reproducing attachment for amplifying the modulated bio-electrical signal reproduced by said magnetic head of said main unit;
a power supply input conductor connected to said power supply output terminals of the reproducing attachment; and
a signal output conductor connected to an output of said amplifier of the reproducing attachment for supplying the modulated bio-electrical signal to the external of the reproducing attachment;

a demodulator energized by an A.C. power source and having an input connected to said signal output conductor of said reproducing attachment for demodulating said modulated bio-electrical signal to produce a demodulated bio-electrical signal which has the same waveform as the bio-electrical signal detected by said detector of said recording attachment;

a D.C. power source connected to said power supply input conductor of said reproducing attachment; and a recorder energized by the A.C. power source and having an input connected to an output of said demodulator for graphically displaying said bio-electrical signal;

whereby only one of said recording and reproducing attachments can be coupled to said main unit at any one time at said side walls by means of said mechanically coupling means.

2. An apparatus as claimed in claim 1, wherein said main unit further comprises a jack provided on said casing of the main unit and connected to the output of said amplifier, and an earphone having a plug capable of being inserted into said jack and having a higher impedance than said magnetic head, whereby the modulated bio-electrical signal to be recorded on said magnetic tape can be monitored by means of said earphone.

3. An apparatus as claim in claim 1, wherein said modulator of said main unit comprises an oscillating circuit for producing a carrier signal of a given frequency and a frequency modulating circuit for frequency modulating said carrier signal with the amplified bio-electrical signal supplied from said amplifier to produce a frequency modulated bio-electrical signal which is recorded on said magnetic tape by means of said magnetic head.

4. An apparatus as claimed in claim 1, wherein said modulator of the main unit comprises an oscillating circuit for producing a carrier pulse signal of a given repetition rate and a modulating circuit for pulse-width modulating said carrier pulse signal with said amplifier bio-electrical signal supplied from said amplifier to produce a pulse-width modulated bio-electrical signal which is recorded on said magnetic tape by means of said magnetic head.

5. An apparatus as claimed in claim 1, wherein said apparatus further comprises an additional attachment to be interposed between said main unit and said recording attachment, said additional attachment including a casing having a first side wall with mechanically coupling means which cooperate with said mechanically coupling means of said main unit to couple said additional attachment to said main unit at their side walls and a second side wall with mechanically coupling means which cooperate with said mechanically coupling means of said recording attachment to couple said recording attachment to said additional attachment at their side walls, signal input terminals provided on said second side wall, said signal input terminals being connected to said signal output terminals of said recording attachment when said recording attachment is coupled to said additional attachment at their side walls, power supply input terminals provided on said second sidewall, said power supply input terminals being connected to said power supply output terminals of said recording attachment when said recording attachment is coupled to said additional attachment at their side walls, signal output terminals provided on said first side wall and connected to said signal input terminals, said signal output terminals being connected to said signal input terminals of said main unit when said additional attachment is coupled to said main unit at their side walls, power supply output terminals provided on said first side wall and connected to said power supply input terminals of the additional attachment, said power supply output terminals being connected to said power supply input terminals of said main unit when said additional attachment is coupled to said main unit at their side walls, a resistor connected across said power supply input terminals through a switch, and a D.C. voltage meter provided on said casing of the additional attachment and connected across said resistor for indicating a voltage level of said battery means installed in said recording attachment when said recording attachment is coupled to said additional attachment at their side walls and said switch is closed.

6. An apparatus as claimed in claim 1, wherein said amplifier provided in said reproducing attachment is formed by a differential amplifier having two inputs, one of which is connected to said signal input terminals of the reproducing attachment and an output which is connected to said signal output conductor of the reproducing attachment, the other input being connected to said output through a resistor, a rectifier connected to said output of said differential amplifier for rectifying a pulsatory signal to produce a rectified pulsatory signal, an integrator connected to said rectifier for integrating said rectified pulsatory signal, a transistor having a base connected to an output of said integrator, an emitter and a collector connected to a reference potential point, a potentiometer connected in series with said emitter of said transistor and having a tap, a field effect transistor having a gate connected to said tap of said potentiometer and a drain-source path connected between said other input of said differential amplifier and said reference potential point, whereby a gain of said differential amplifier is controlled to maintain peak values of the amplified pulsatory signal supplied from the differential amplifier to the constant.

7. An apparatus as claimed in claim 1, wherein said apparatus further comprises an additional attachment to be interposed between said main unit and said recording attachment, said additional attachment including a casing having a first side wall with mechanically coupling means which cooperate with said mechanically coupling means of said main unit to couple said additional attachment to said main unit at their side walls and a second side wall with mechanically coupling means which cooperate with said mechanically coupling means of said recording attachment to couple said recording attachment to said additional attachment at their side walls, signal input terminals provided on said second side wall, said signal input terminals being connected to said signal output terminals of said recording attachment when said recording and additional attachments are coupled together at their side walls, power supply input terminals provided on said second side wall, said power supply input terminals being connected to said power supply output terminals of said recording attachment when said recording and additional attachments are coupled together at their side walls, signal output terminals provided on said first side wall and connected to said signal input terminals of the additional attachment, said signal output terminals being connected to said signal input terminals of said main unit when said additional attachment and main unit are coupled together at their side walls, power supply output terminals provided on said second side wall and connected to said power supply input terminals of said additional attachment, said power supply output terminals being connected to said power supply input terminals of said main unit when said additional attachment and main unit are coupled together at their side walls, an electric battery, and additional power supply output terminals provided on said second side wall of the additional attachment and connected across said battery, and said recording attachment further comprises additional power supply input terminals provided on said side wall of the recording attachment, said additional power supply input terminals being connected to said additional power supply output terminals of said additional attachment when said recording and additional attachments are coupled together at their side walls, said detector of the recording attachment is formed by a bridge circuit of wire resistance strain gauge to which said additional power supply input terminals of the additional attachment are connected through said electrical conductor.

8. An apparatus as claimed in claim 1, wherein said main unit further comprises a large capacitor for cutting a D.C. component and having one electrode connected to the output of said amplifier of the main unit and the other electrode connected to the input of said modulator, a transistor having an emitter-collector path connected between said other electrode of said large capacitor and a reference potential point, and a timing circuit consisting of a resistor and a capacitor and connected to a base of said transistor for making said transistor conductive for a given time period at an instance when said main unit is energized so as to charge quickly said large capacitor.

9. An apparatus as claimed in claim 1, wherein said power supply input terminals of said main unit are composed of two sets of terminals, one set of terminals being connected to said amplifier and modulator and the other set of terminals being connected to said tape driving means, said power supply output terminals of said recording attachment include two sets of terminals, each of which is connected to each of said two sets of terminals of said main unit when said recording attachment and main unit are coupled together at their side walls, and said power supply output terminals of said reproducing attachment are composed of one set of terminals which is connected to said other set of terminals of said main unit when said reproducing attachment and main unit are coupled together at their side walls, whereby when said recording attachment and main unit are coupled together at their side walls, all of said amplifier, modulator and tape driving means of said main unit are energized, but when said reproducing attachment and main unit are coupled together at their side walls, only said tape driving means of said main unit are energized.

10. An apparatus as claimed in claim 1, wherein said apparatus further comprises an additional attachment to be interposed between said main unit and said recording attachment, said additional attachment comprising a casing having a first side wall with mechanically coupling means which cooperate with said mechanically coupling means of said main unit to couple said additional attachment to said main unit at their side walls and a second side wall with mechanically coupling means which cooperate with said mechanically coupling means of said recording attachment to said additional attachment at their side walls, signal input terminals provided on said second side wall and being connected to said signal output terminals of said recording attachment when said recording attachment is coupled to said additional attachment, power supply input terminals provided on said second side wall, said power supply input terminals being connected to said power supply output terminals of said recording attachment when said recording attachment is coupled to said additional attachment, signal output terminals provided on said first side wall and connected to said signal input terminals of the additional attachment through a first switch, said signal output terminals being connected to said signal input terminals of said main unit when said additional attachment is coupled to said main unit, a calibration voltage pulse generating circuit connected to said power input terminals through a second switch and having an output connected to said signal output terminals through said first switch, and an operating member provided on said casing of the additional attachment for actuating said first and second switches, whereby when said operating member is actuated, said first and second switches are driven in such positions that said calibration voltage pulse generating circuit is energized to produce calibration voltage pulses having a given amplitude and a given repetition rate and said calibration voltage pulses are supplied through said first switch to said signal output terminals of the additional attachment.

11. An apparatus as claimed in claim 10, wherein said calibration voltage pulse generating circuit comprises a mono-stable multivibrator having an input connected to said power supply input terminals through said second switch and producing a pulse series having a given pulse width and a given repetition rate, a constant current source connected to an output of said mono-stable multivibrator and driven by said pulse series from said mono-stable multivibrator to produce a constant current pulse series having said given repetition rate, and a resistor connected to an output of said constant current source to pass said constant pulse series therethrough so as to produce said calibration voltage pulses having a given constant amplitude and said given repetition rate.

12. An apparatus as claimed in claim 1, wherein said recording attachment further comprises a remote control switch including a casing which is coupled to said casing of the recording attachment through an electric conductor, switch contacts which are disposed in said casing of the remote control switch and are electrically connected between said battery means and said power supply output terminals of said recording attachment by means of said electric conductor, and an operating member provided on said casing of the remote control switch for actuating said switch contacts.

13. An apparatus as claimed in claim 12, wherein said remote control switch further comprises
   an electric battery,
   a resistor connected across said battery through switch contacts,
   an operating member provided on said casing of the remote control switch for actuating said switch contacts, and
   means for applying a voltage produced across said resistor to said signal output terminals of said recording attachment, whereby said operating member is repeatedly actuated and voltage pulses produced across said resistor are applied to said signal output terminals of said recording attachment as the calibration voltage pulses.

14. An apparatus as claimed in claim 12, wherein said apparatus further comprises an additional attachment to be interposed between said main unit and said recording attachment, said additional attachment including
   a casing having a first side wall with mechanically coupling means which cooperate with said mechanically coupling means of said main unit to couple said additional attachment to said main unit at their side walls and a second side wall with mechanically coupling means which cooperate with said mechanically coupling means of said recording attachment to couple said recording attachment to said additional attachment at their side walls,
   signal input terminals provided on said second side wall, said signal input terminals being connected to said signal output terminals of said recording attachment when said recording attachment is coupled to said additional attachment,
   power supply input terminals provided on said second side wall, said power supply input terminals being connected to said power supply output terminals of said recording attachment when said recording attachment is coupled to said additional attachment,
   signal output terminals provided on said first side wall and connected to said signal input terminals of the additional attachment through a first switch, said signal output terminals being connected to said signal input terminals of said main unit when the additional attachment is coupled to said main unit,
   a calibration voltage pulse generating circuit connected to said power supply input terminals through a second switch and having an output connected to said signal output terminals through said first switch, and
   a timing circuit connected to power supply input terminals and including a relay coil which actuates said first and second switches,
   whereby when said recording attachment, additional attachment and main unit are coupled together and said remote control switch is is actuated, said timing circuit is energized for a given time period to energize said relay coil so as to actuate said first and second switches in such a manner that said calibration voltage pulse generating circuit is energized through said second switch to produce calibration voltage pulses having a given amplitude and a given repetition rate and the calibration voltage pulses are applied to said signal output terminals of the additional attachment through said first switch and after said given time period relay coil of said timing circuit is deenergized so that said calibration voltage pulse generating circuit is deenergized and said signal input terminals are connected to said signal output terminals through said first switch.

15. An apparatus as claimed in claim 14, wherein said calibration voltage pulse generating circuit comprises
   a mono-stable multivibrator having an input connected to said power supply input terminals through said second switch and producing a pulse series having a given pulse width and a given repetition rate,
   a constant current source connected to an output of said mono-stable multivibrator and driven by said pulse series from said mono-stable multivibrator to produce a constant current pulse series having said given repetition rate, and
   a resistor connected to an output of said constant current source to pass said constant pulse series therethrough so as to produce said calibration voltage pulses having a given constant amplitude and said given repetition rate.

* * * * *